United States Patent
Houde et al.

(10) Patent No.: US 7,267,667 B2
(45) Date of Patent: Sep. 11, 2007

(54) FLUID MANAGEMENT SYSTEM FOR CORONARY INTERVENTION

(75) Inventors: Eric Houde, Saratoga Springs, NY (US); Mark VanDiver, Argyle, NY (US); Colin P. Hart, Queensbury, NY (US); Valerie M. Castora, Fort Ann, NY (US); Kathryn M. Albert, Saratoga Springs, NY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 771 days.

(21) Appl. No.: 10/193,376

(22) Filed: Jul. 11, 2002

(65) Prior Publication Data

US 2004/0010229 A1    Jan. 15, 2004

(51) Int. Cl.
*A61M 1/00* (2006.01)
(52) U.S. Cl. .................. 604/154; 604/151; 600/432
(58) Field of Classification Search ........ 600/431–433; 604/191, 151–155
See application file for complete search history.

(56) References Cited

U.S. PATENT DOCUMENTS

| | | | |
|---|---|---|---|
| 3,888,239 A | * | 6/1975 | Rubinstein ................. 600/432 |
| 5,450,847 A | | 9/1995 | Kampfe et al. |
| 5,592,940 A | | 1/1997 | Kampfe et al. |
| 5,806,519 A | | 9/1998 | Evans, III et al. |
| 6,221,045 B1 | * | 4/2001 | Duchon et al. ............. 604/151 |
| 6,471,674 B1 | * | 10/2002 | Emig et al. ................. 604/131 |

FOREIGN PATENT DOCUMENTS

| | | |
|---|---|---|
| DE | 198 59 811 A1 | 6/2000 |
| EP | 0 576 740 A1 | 1/1994 |
| EP | 1 090 650 A1 | 4/2001 |
| WO | WO-99/21600 | 5/1999 |
| WO | WO-01/80928 A2 | 11/2001 |

* cited by examiner

*Primary Examiner*—Catherine S. Williams
(74) *Attorney, Agent, or Firm*—Miller, Matthias & Hull

(57) ABSTRACT

A fluid injection system is disclosed The system is adapted to employ first and second injectors which may sequentially, or simultaneously, inject first and second fluids into a patient via a catheter. The first and second injectors may be power actuated. The actuation of the injectors may be controlled via a controller of the system. The user may be provided with an operator interface module to enable the control of the system to be affected during operation. A separate waste line may be provided to drain the system effectively and efficiently. A pressure sensor may be provided proximate the catheter to reduce pressure signal wave dampening and fluid waste.

25 Claims, 5 Drawing Sheets

FLUID MANAGEMENT SYSTEM FOR CORONARY INTERVENTION

FIELD OF THE DISCLOSURE

The disclosure generally relates to fluid dispensing machines and, more particularly, relates to fluid dispensing machines for use with power actuated syringes.

BACKGROUND OF THE DISCLOSURE

During medical procedures, fluids of different types need to be injected into human tissue and vascular structures. One such procedure is known as angiography. Angiography is a procedure used in the detection and treatment of abnormalities or restrictions in blood vessels, heart chambers and heart valves. During angiography, a radiographic image of a vascular structure is obtained by injecting radiographic contrast material through a catheter into such a vessel, heart chamber, or heart valve. X-rays are then passed through the region of the body in which the contrast material was injected. The X-rays are absorbed by the contrast material causing a radiographic outline or image of the blood vessel containing the contrast material. The x-ray images of the blood vessels filled with the contrast material are usually recorded on the film or videotape and displayed on a fluoroscope monitor.

The injection of the contrast or other fluids can be performed either manually or automatically. In both procedures, a catheter is inserted into a vessel, which in turn is connected to a fluid line leading to a manifold and in turn to an injector or syringe. The plunger of the syringe is then either manually or automatically depressed to inject fluid through the fluid line, the catheter, and into the patient.

In certain situations, it is necessary to dilute the concentration of contrast being injected into a patient. For example, in those patients with renal insufficiency incapable of processing concentrated contrast through their system, or in cases where a large amount of contrast is used, such as complicated coronary interventions (PTCA) or peripheral (PTA) cases with runoffs, direct injections of contrasts, are not possible. Accordingly, it is necessary to mix the contrasts and saline prior to injection to arrive at the appropriate dilution percentage. Such processes are necessarily slow and are currently difficult to achieve.

In addition, during injections, it is desirable for the physician or technician to be provided with feedback as to the pressure within the vessel. This is commonly provided by way of a pressure transducer mounted relatively close to the injection apparatus. However, since a relatively long expanse of conduit exists between the catheter and the injector, typically on the order of four feet or more, pressure waveforms must be transmitted through the fluid contained within that conduit all the way from the body of the patient, through the catheter, and back to the pressure transducer. Due to such distances, the waveforms may be substantially dampened by the time they reach the transducer thereby providing an inaccurate or poor signal for display to the physician.

Furthermore, after an injection is made, and it is desired to remove the contrast from the injection system or change the fluid being injected, it is currently necessary to evacuate or aspirate the entire injection line. It would be advantageous if the waste could be quickly removed, while at the same time limiting the total volume of waste fluid encountered by the system.

SUMMARY OF THE DISCLOSURE

In accordance with one aspect of the disclosure, an injection system is provided which comprises a first power actuated injector, a second power actuated injector, a fitting, and a catheter. The first power actuated injector is adapted to inject a first fluid through a first fluid line having a distal end, and the second power actuated injector is adapted to inject a second fluid through a second fluid line having a distal end. The fitting has first and second inputs and an output, with the distal ends of the first and second fluid lines being connected to the first and second inputs of the fitting, respectively. The catheter is connected to the fitting output.

In accordance with another aspect of the disclosure, a method of injecting fluid is provided which comprises the steps of providing a first power actuated injector, providing a second power actuated injector, connecting first and second fluid lines to a single catheter, and actuating one of the first and second power actuated injectors. The first power actuated injector is adapted to transport a first fluid from a first receptacle through the first fluid line, while the second power actuated injector is adapted to transport a second fluid from a second receptacle through the second fluid line.

These and other aspects and features of the disclosure will become more apparent upon reading the following detailed description in conjunction with the accompanying drawings.

Figure 1:
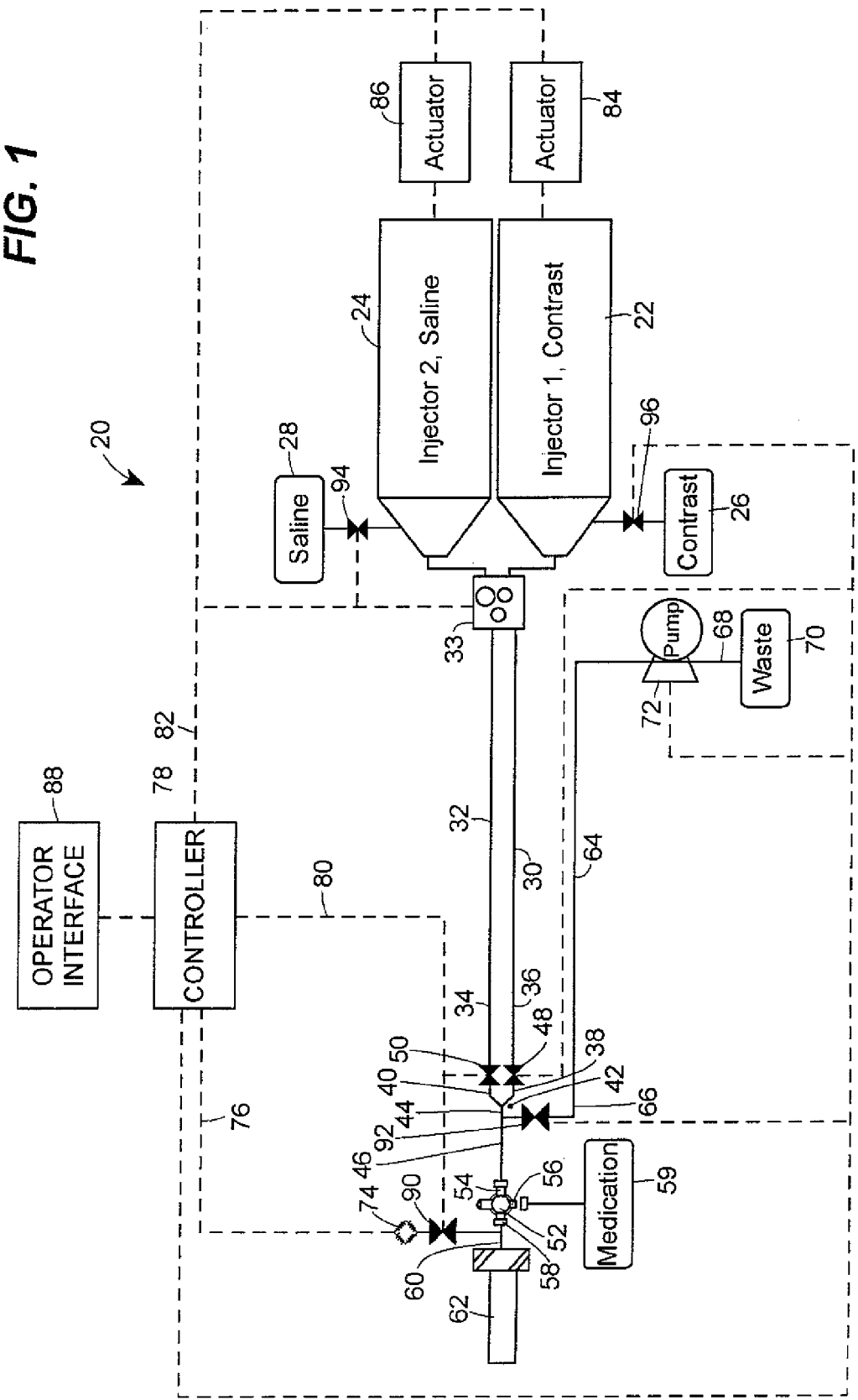
FIG. 1 is a schematic representation of an injection system constructed in accordance with the teachings of the disclosure.

While the disclosure is susceptible to various modifications and alternative constructions, certain illustrative embodiments thereof have been shown in the drawings and will be described below in detail. It should be understood, however, that there is no intention to limit the disclosure to the specific forms disclosed, but on the contrary, the intention is to cover all modifications, alternative constructions, and equivalents falling within the spirit and scope of the disclosure as defined by the appended claims.

DETAILED DESCRIPTION

Referring now to the drawings, an injection system constructed in accordance with the teachings of the disclosure is generally depicted by reference numeral 20. While the system 20 is described herein in conjunction with angiographic procedures wherein radiopaque contrast is utilized, it is to be understood that the teachings of the disclosure can be utilized to construct injection systems for any other type of fluid as well. In the paragraphs that follow, the relative positions of the components of the system 20 will be described in terms of being "upstream" or "downstream"

from one another. It is to be understood that if two components A and B are provided with component A being closer to a patient, component A is said to be "downstream" of component B, and component B is said to be "upstream" of component A.

The injection system 20 includes, in the first embodiment of FIG. 1, a first injector 22 and a second injector 24 adapted to draw fluid from a first fluid supply 26 and a second fluid supply 28, respectively. In the depicted embodiment, the first fluid supply 26 may be a supply of contrast while the second fluid supply 28 may be a supply of saline. The saline and contrast are directed by the first and second injectors 22, 24 through first and second fluid lines 30 and 32, respectively. A bubble detector 33 may be provided to detect and/or remove gas entrained in the liquid of supplies 26 and 28. As used herein, solid lines are provided in the figures to illustrate fluid connections, while dashed lines are used to illustrate electrical connections.

The first and second fluid lines 30, 32 include distal ends 34, 36, respectively, which may terminate at first and second inputs 38, 40, respectively, of a Y-shaped fitting 42. The Y-shaped fitting 42 further includes an outlet 44 connected to an output conduit 46. An advantage of using such a fitting having multiple inlets and one outlet is that multiple fluids can be supplied under pressure from multiple sources and be mixed in the fitting 42 prior to injection. Accordingly, the injected fluid can be tailored in terms of viscosity, concentration, etc., during the procedure without requiring pre-mixing of same as is required by the prior art. Control valves 48 and 50 may be provided within the first and second fluid lines 30, 32, respectively. It is to be understood that the fitting 42 need not be Y-shaped, and that in alternative embodiments may be T-shaped, or otherwise shaped to allow coupling of fluid lines as would be contemplated by one skilled in the art. Moreover, the control valves 48 and 50 may be provided in a variety of forms such as, but not limited to, check valves, pinch valves, or any other type of valve contemplated by one skilled in the art.

The output conduit 46 terminates at a valve 52 having first and second inputs 54, 56 and an output 58. The input 54 is connected to the output conduit 46. The input 56 is connected to a medication supply 59. The output 58 is connected to a conduit 60 which leads to a medical device 62 which may be a catheter, or the like.

Also depicted in FIG. 1 is a waste line 64 having an input 66 connected to the output conduit 46, and an output 68 connected to a waste receptacle 70. A pump 72 is operatively associated with the waste line 64 to draw fluid from the output conduit 46 and any fluid lines fluidically connected to the output conduit 46. It can therefore be seen that separate lines 30, 32 and 64 are supplied for the contrast, saline, and waste, respectively. This is advantageous in that when it is desired, for example, to inject saline after injecting contrast, and injection can occur immediately without first clearing the system of contrast from the prior injection. This is in direct opposition to the prior art wherein the contrast existing in the line (e. g., 4-5 ccs of fluid) would have to first be injected into the patient, or cleaned, prior to saline injection. Moreover, by providing the waste line 64 close to the medical device 62, when the device 62 is to be drained of waste, it can be done quickly and with far less waste. Put another way, since prior art systems drain the device using a pump (run in reverse) mounted back by the injector, not only must the device be drained with prior art systems, but the entire line connecting the injector to the device must be drained as well, which is overcome by the present disclosure. This represents not only a large volume (e. g., 4-5 ccs) of waste, but a source of delay as well.

A pressure sensor 74 may be positioned proximate the catheter 62. The pressure sensor 74 is shown connected to the catheter conduit 60. An advantage of positioning the pressure transducer 74 close to the catheter 62 is that, unlike prior art systems, the pressure waveforms need not be communicated all the way down the line to the injector and thus be subjected to substantial waveform dampening, but rather can be monitored before such dampening can occur and thus result in a much more accurate signal. The pressure sensor 74 generates a signal 76 representative of fluid pressure within the output conduit 46. The signal 76 is communicated to a controller 78 which in turn generates a display signal 78 for transmission to an operator interface module 79, enabling the physician or technician to monitor pressure.

In alternative embodiments, the pressure signal 76 may be used by the controller 78 in determining or modifying control signals 80, 82 for controlling actuators 84 and 86 connected to the first and second injectors 22 and 24, respectively. The actuators 84 and 86 may be any suitable actuating device such as, but not limited to, motor driven, hydraulically powered, or pneumatically powered plungers. However, it is to be understood that the control signals 80, 82 are primarily generated by the operator depressing or otherwise actuating buttons, keypads, or the like for varying the ratio of a first fluid (e. g., contrast) to a second fluid (e. g., saline), and that the pressure signal 76 is provided mainly to enable the physician to monitor pressure.

The operator interface module 88 is associated with the controller 78 to enable a user to affect operation of the system 20 and provide the user with valuable feedback as to the operation of the system 20. For example, the operator interface module 88 may include a display screen such as a glass plasma, liquid crystal, or cathode ray tube display, or the like, and/or a plurality of input/output devices such as the aforementioned keypad, buttons, mouse or the like for entering and receiving data. The controller may be electrically connected to valves 48, 50, 90, 92, 94, and 96 to monitor the valves, or control movement of fluid flow directions.

In operation, the system 20 is able to inject fluid or fluids through the catheter 62 and into a patient (not shown). By employing the first and second injectors 22 and 24, first and second fluids, such as saline and contrast, can be sequentially injected with substantially no down time for the system 20. In addition, the saline and contrast can be simultaneously injected by simultaneously operating the first and second injectors 22. This in turn forces saline and contrast into the fitting 42 and automatically mixes the fluids. Moreover, as opposed to existing systems which employ a single injector for contrast and a peristaltic pump for saline/flushing, the separate injector dedicated to saline injection enables smooth flow without the pulsating flow associated with peristaltic pumps.

When the system is to be drained, the separate waste line 64 can be utilized along with pump 72 to quickly and efficiently draw fluid out of the system 20 and ready the system 24 for additional injections. By providing the pressure sensor 74 proximate the catheter 62, the signal 76 representative of fluid pressure within the catheter conduit 60 is more accurate and less susceptible to wave dampening.

Figure 2:
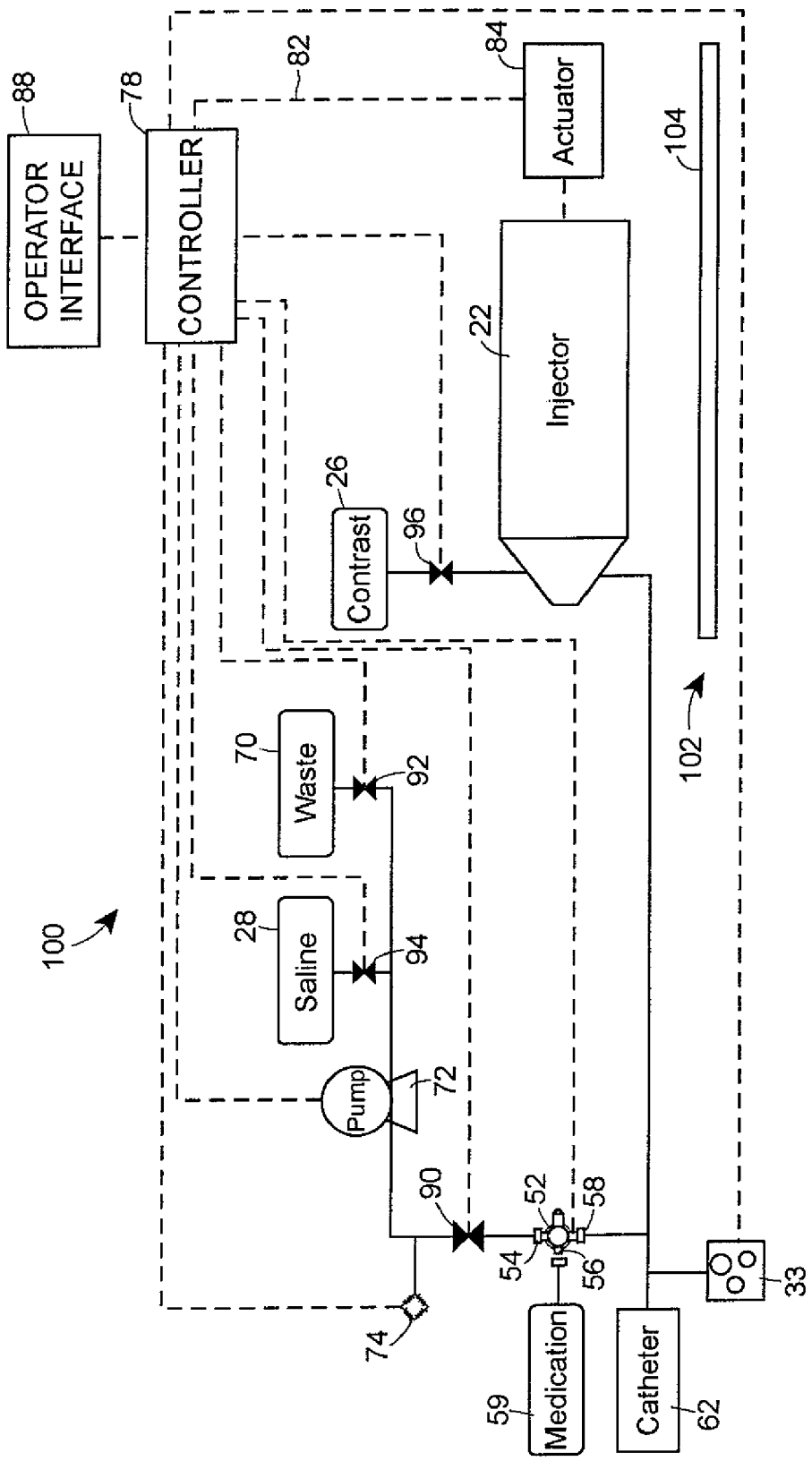
FIG. 2 is a schematic representation of an injection system constructed in accordance with the teachings of the disclosure.

Referring now to FIG. 2, an alternative embodiment of an injection system is generally referred to by reference numeral 100. Wherein like elements are utilized, like reference numerals are employed. A difference in the alternative embodiment is that only a single injector 22 is employed. More specifically, the injector 22 is used to inject contrast, in the depicted embodiment, while the saline is injected by the peristaltic pump 72 run in reverse.

FIG. 2 also depicts a possible position of the injector 22 and actuator 84 relative to an operating table 102. As shown therein, the injector 22 and actuator may be proximate the table 102, i.e., on an underside 104 thereof. In so doing, the system 100 is made more efficient in that the supply lines of the system 100 can be made shorter, thereby reducing the amount of contrast or other fluid needed in the system. Such placement of the injector and other equipment of the system can be employed with the first embodiment with equal efficacy.

With regard to the actual valves used to control fluid flow through the various fluid lines, any number of valve types, including but not limited to check valves, high pressure valves, rotary manifold valves, pinch valves and the like could be employed. In the embodiment of FIGS. 3-7, a pinch valve system is disclosed. FIGS. 3-7 also depict one potential type of user control incorporated within the operator interface 88.

Figure 3:
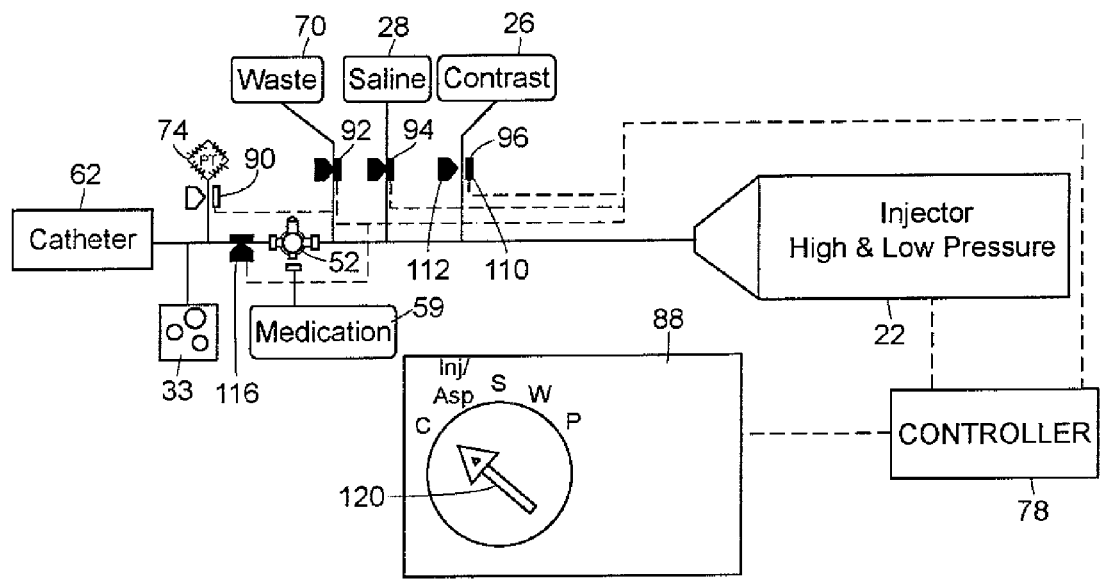
FIG. 3 is a schematic representation of an injection system in a first position.

Beginning with FIG. 3, it will be noted that each valve is depicted as a pinch valve, meaning the valve includes an anvil 110, and a movable wedge 112 adapted to move toward and away from the anvil 110 as by a pneumatic/hydraulic cylinder, motor or the like to pinch a flexible tube (forming the fluid line) therebetween and thus prevent fluid flow. It is to be understood that other types of pinch valves, such as those employing multiple movable elements adapted to move toward one another, are possible. For example, in FIG. 3, the contrast valve 96 is depicted in an open position, with the waste valve 92, saline valve 94, and an output valve 116 shown closed. The pressure valve 90, as described herein, is always open except during injection (FIG. 4) to provide the user with a constant pressure reading.

Figure 4:
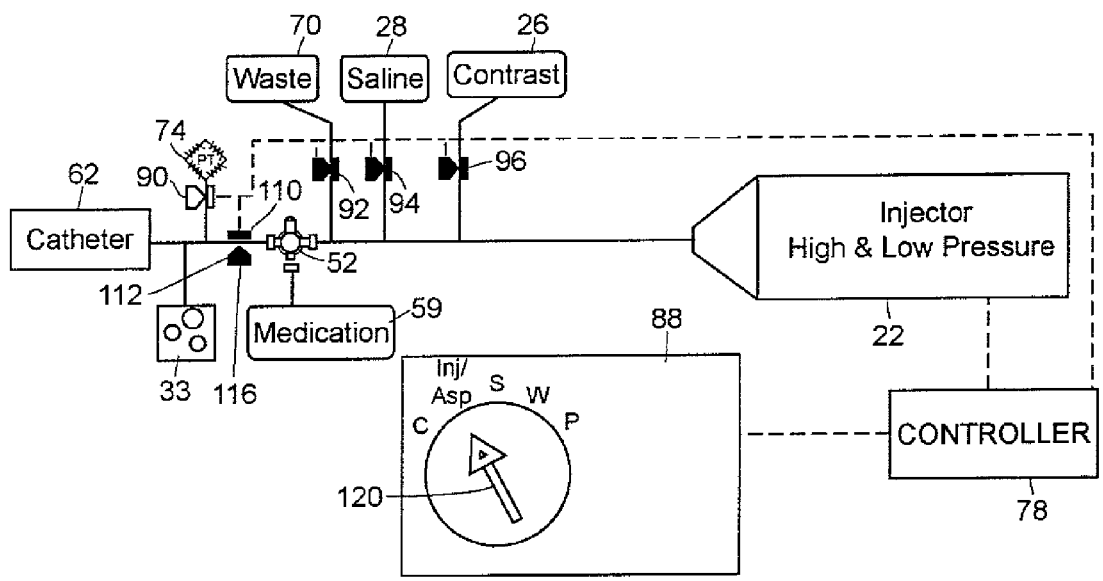
FIG. 4 is a schematic representation of an injection system in a second position.

With the contrast valve 96 open, the injector 22 can retract, thereby drawing contrast from supply 26, through the valve 96 and into the injector 22. The user can then adjust a control unit 120 of the operator interface 88 to specify injection as shown in FIG. 4, whereupon the contrast valve 96 is closed and the output valve 116 is opened. The injector plunger (not shown) can then advance, thereby pushing contrast from the injector 22 to the catheter 62 and patient.

Figure 5:
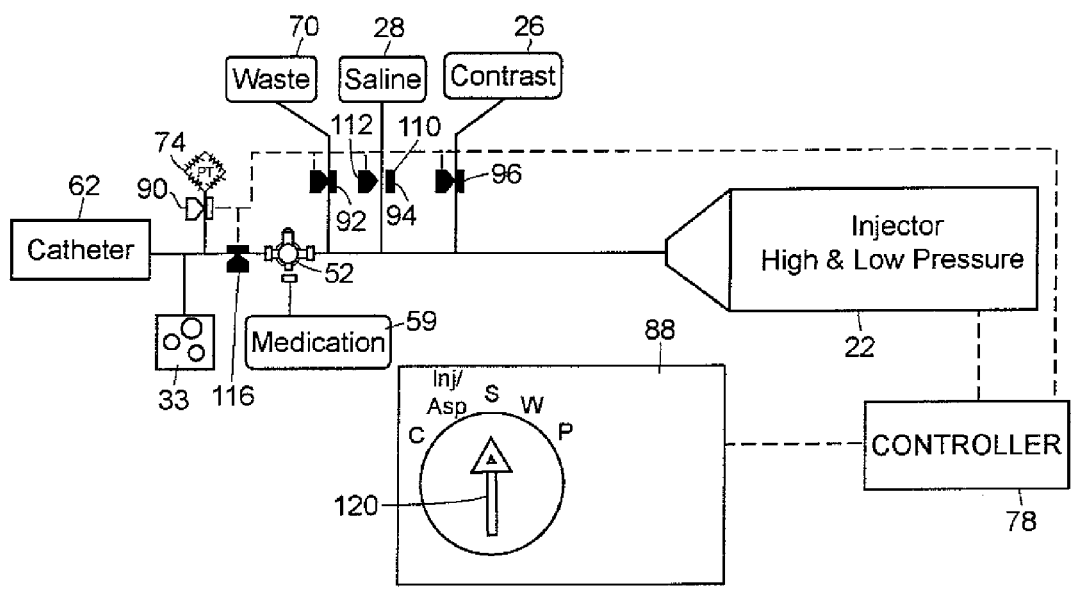
FIG. 5 is a schematic representation of an injection system in a third position.
Figure 6:
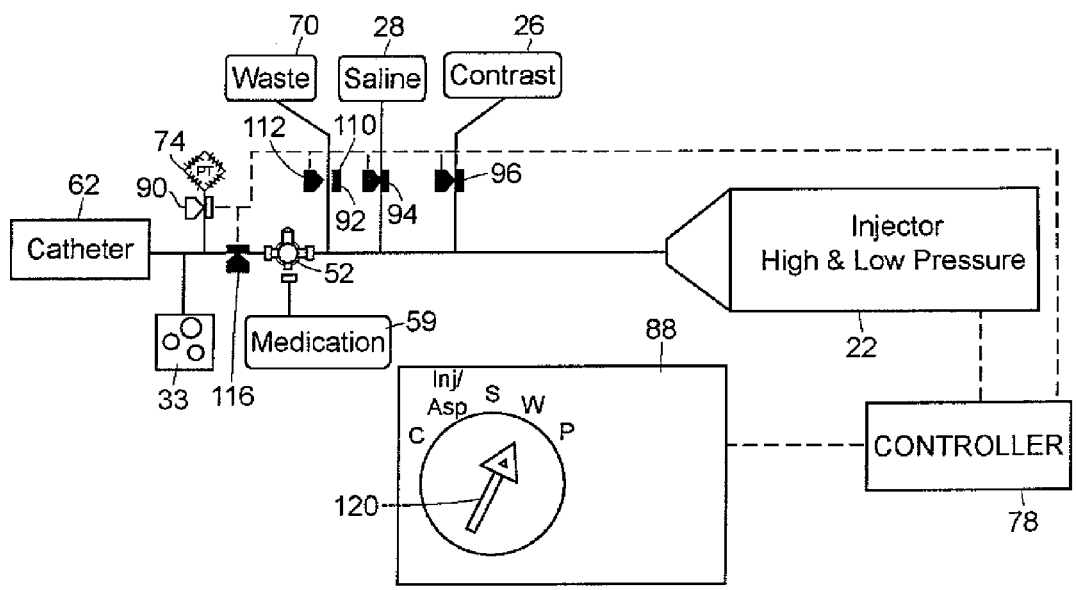
FIG. 6 is a schematic representation of an injection system in a fourth position.
Figure 7:
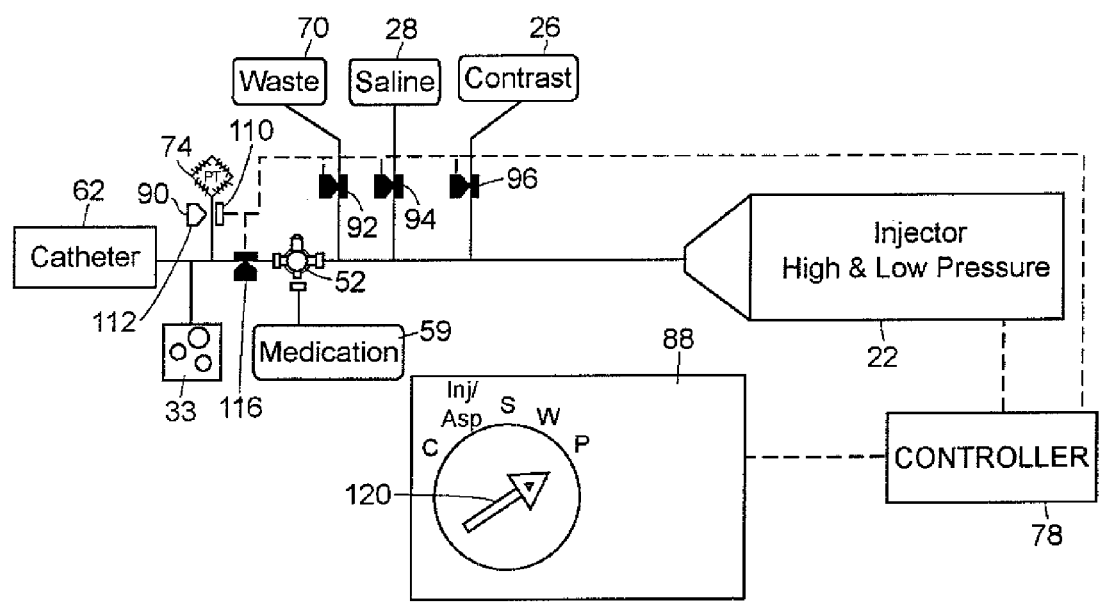
FIG. 7 is a schematic representation of an injection system in a fifth position.

FIGS. 5-7 are much the same, but with the control unit 120 moved to positions corresponding to saline, waste, and pressure, respectively, with the corresponding valve (94, 92, 90) being depicted in an open position when selected with the control unit 120. It is to be understood that the control unit 120 need not be provided by way of the rotary knob depicted but could be any other suitable mechanism enabling a setting to be selected and a corresponding valve signal to be generated. This may include, but not be limited to push buttons and toggle switches, or non-handheld units such as monitor touch screens, and the like. The valve signal generated could be used to actuate a motor (not shown) for moving the wedge 112, energizing a solenoid, pressurizing a hydraulic or pneumatic cylinder, releasing a spring, or the like. Moreover, the signal could be used to manipulate the valve such that vacuum pressure created by the retracting plunger of the injector 22 could cause the desired valve to open. For example, the valves could be provided as normally closed valves wherein the actuation of a solenoid holds the valve open. The control signal could actuate the solenoid so as to release the valve, allowing only a spring or the like to hold the valve closed. The spring could be sized such that the vacuum pressure created by the retracting injector plunger could overcome the spring force and thereby open the valve. Other systems are certainly possible.

From the foregoing, one of ordinary skill in the art will appreciate that the present disclosure sets forth an apparatus and method for managing fluids injected and otherwise used in a medical procedure.

What is claimed is:

1. An injection system, comprising:
   a first power-actuated injector adapted to inject a first fluid through a first fluid line having a distal end;
   a second power-actuated injector adapted to inject a second fluid through a second fluid line having a distal end;
   a fitting having first and second inputs and an output, the distal ends of the first and second fluid lines being connected to the first and second inputs of the fitting, respectively;
   a medical device connected to the fitting output through a third fluid line; and
   a pressure sensor connected to the third fluid line at downstream of the fitting and adapted to generate a signal representative of fluid pressure within the medical device.

2. The injection system of claim 1, wherein the medical device is a catheter.

3. The injection system of claim 1, wherein the first fluid is contrast and the second fluid is saline.

4. The injector system of claim 1, wherein the fining is Y-shaped.

5. The injection system of claim 1, further including a waste line having a proximal end and a distal end, the distal end being connected to the third fluid line downstream of the fitting.

6. The injection system of claim 5, further including a waste receptacle connected to the distal end of the waste line and a pump operatively associated with the waste line.

7. The injection system of claim 6, further including a valve downstream of the distal end of the waste line.

8. The injection system of claim 1, wherein the pressure sensor is connected to the third fluid line upstream of the medical device.

9. The injection system of claim 7, further including a medication in communication with the valve.

10. A method of injecting fluid into a patient, comprising:
    providing a first power-actuated injector adapted to transport a first fluid from a first receptacle through a first fluid line;
    providing a second power actuated injector adapted to transport a second fluid from a second receptacle through a second fluid line;
    connecting the first and second fluid lines to a single catheter;
    providing a pump adapted to transport fluid from the catheter, first fluid line, and second fluid line to a waste receptacle actuating one of the first and second power-actuated injectors; and
    monitoring pressure using a transducer mounted proximate the catheter.

11. The method of claim 10, wherein the first fluid is contrast and the second fluid is saline.

12. The method of claim 10, wherein the first and second fluid lines are connected using a Y-fitting.

13. The method of claim 10, further including actuating the first and second injectors simultaneously.

14. An injection system, comprising:
    a first power-actuated injector;

a second power-actuated injector;

a catheter;

a fitting having an output and first and second inputs, the output being connected to the catheter; the first and second inputs being connected to the first and second injectors;

a waste line and a pump operatively associated with the waste line, the waste line having an input in fluid communication with the fitting a pressure transducer positioned proximate the catheter and adapted to generate a signal representative of fluid pressure within the catheter; and a controller adapted to receive signals and generate control signals for actuation of the first and second power actuated injectors.

15. The injection system of claim 14, further including a source of medication in fluid communication with the catheter.

16. The injection system of claim 14, further including a source of contrast in fluid communication with the first power-actuated injector; and a source of saline in fluid communication with the second power-actuated injector.

17. An injection system, comprising:

an injector;

a medical device;

a fluid line connecting the medical device and the injector;

a waste line and a pump operatively associated with the waste line, the waste line being connected to the fluid line;

a pressure sensor connected to the fluid line downstream of the waste line and adapted to generate a signal representative of fluid pressure within the medical device; and a controller adapted to receive a signal and generate a control signal for controlling the flow of fluid from the injector.

18. The injection system of claim 17, wherein the medical device is a catheter.

19. The injection system of claim 17, further including a power driven actuator connected to a plunger of the injector and wherein the control signal determines movement of the plunger.

20. The injection system of claim 17, further including a valve operatively associated with an output of the injector; and wherein the control signal determines movement of the valve.

21. The injection system of claim 17, further including a second injector and a second fluid line, the second fluid line connecting the second injector to the catheter.

22. The injection system of claim 21, wherein the first injector is fluidically connected to a source of contrast, and wherein the second injector is fluidically connected to a source of saline.

23. An injection system, comprising:

a power-actuated injector;

a medical device;

a fluid line connecting the medical device and the injector;

a waste line connected to the fluid line;

a pressure sensor connected to the fluid line downstream of the waste line and adapted to generate a signal representative of fluid pressure within the medical device;

a pump operatively associated with the waste line and adapted to draw fluid from the medical device fluid line and injector;

a second power actuated injector and a second fluid line, the second fluid line connecting the second power actuated injector to the medical device;

and a third fluid line connected to a medication.

24. The injection system of claim 23, wherein the medical device is a catheter.

25. The injection system of claim 23, further including a controller adapted to generate signals for operation of the power-actuated injector and pump.

* * * * *